United States Patent [19]

Barlow, Jr. et al.

[11] 4,338,950

[45] Jul. 13, 1982

[54] SYSTEM AND METHOD FOR SENSING AND MEASURING HEART BEAT

[75] Inventors: Carl A. Barlow, Jr.; Lee R. Reid, both of Plano, Tex.

[73] Assignee: Texas Instruments Incorporated, Dallas, Tex.

[21] Appl. No.: 189,400

[22] Filed: Sep. 22, 1980

[51] Int. Cl.³ .............................................. A61B 5/02
[52] U.S. Cl. .................................... 128/687; 128/782
[58] Field of Search ........................ 128/670, 687–690, 128/782

[56] References Cited

U.S. PATENT DOCUMENTS

| | | | |
|---|---|---|---|
| 4,157,708 | 6/1979 | Inura | 128/666 |
| 4,202,350 | 5/1980 | Walton | 128/690 |
| 4,211,237 | 7/1980 | Nagel | 128/698 |
| 4,258,719 | 3/1981 | Lewyn | 128/690 |
| 4,280,506 | 7/1981 | Zurcher | 128/690 |

FOREIGN PATENT DOCUMENTS 2848198  5/1980  Fed. Rep. of Germany ...... 128/690

*Primary Examiner*—Kyle L. Howell
*Assistant Examiner*—Francis J. Jaworski
*Attorney, Agent, or Firm*—Melvin Sharp; Leo N. Heiting; Robert D. Marshall, Jr.

[57] ABSTRACT

An improved system and method for sensing and measuring heart beat. A body-mountable instrument is provided having a first sensor for detecting pulsing of a user's blood resulting from the user's heart beat and body movement and generating a first electrical signal indicative thereof and a second sensor for detecting the user's body movement and generating a second electrical signal indicative thereof. The instrument further includes a processor responsive to the first and second electrical signals for determining the period of the second electrical signal and for subtracting a first portion of the first electrical signal occurring during a first time interval from a corresponding portion of the first electrical signal occurring during a second time interval. The second time interval is separated from the first time interval by a time period nt, where n is an integer and t is the period of the second electrical signal, so that the body movement component is removed from the first electrical signal, yielding the true heart beat signal.

23 Claims, 11 Drawing Figures

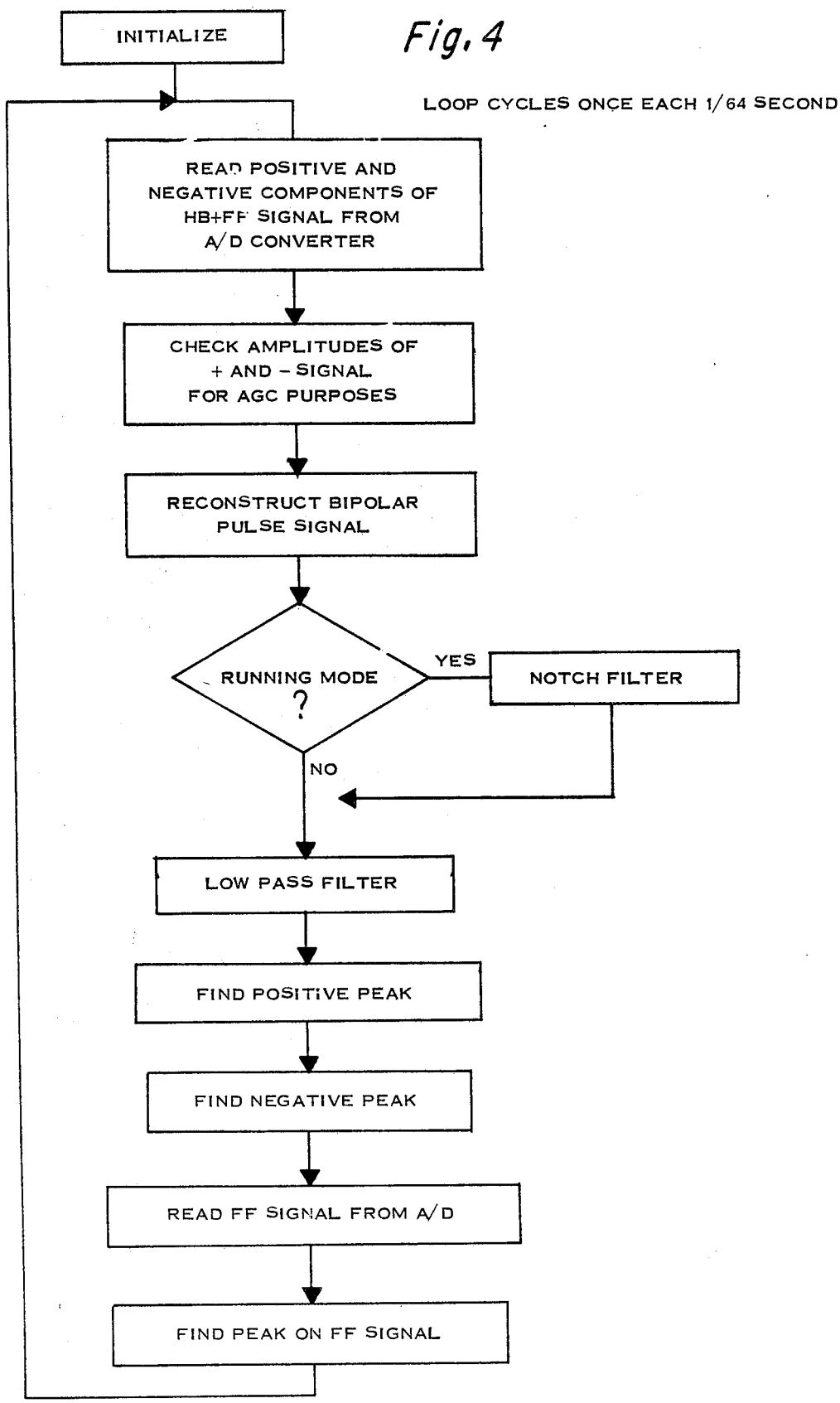

SYSTEM AND METHOD FOR SENSING AND MEASURING HEART BEAT

BACKGROUND OF THE INVENTION

This invention relates to physiological measuring instruments and in particular to a body-mountable instrument for sensing and measuring heart beat. This invention further relates to U.S. Pat. No. 4,312,358, which is assigned to the assignee of the present invention.

Instruments for measuring physiological parameters such as heart beat and the like are known in the art. Some of these instruments employ electrocardiogram (EKG) electrodes to sense heart beat, as exemplified by U.S. Pat. No. 3,792,700. EKG pick up electrodes, however, are often cumbersome and inconvenient to use, particularly for persons engaged in physical exercise. Other physiological measuring instruments use pressure sensors to detect pulsing of blood and transducers to convert such pressure pulses to electrical pulses, as exemplified by U.S. Pat. No. 3,742,937. Pressure sensors are typically more conducive to portable, miniature heart beat measuring instruments than EKG electrodes because only a single sensor is required instead of two separately disposed electrodes.

A major problem associated with prior art heart beat measuring instruments is the problem of accurately measuring the heart beat of one who is engaged in vigorous physical activity because of the background noise associated with body movement during exercise. Periodic body motion associated with the user's feet hitting the ground and his arms swinging back and forth during exercise will cause the user's blood to pulse, particularly in extremities such as the hands and feet, and will be detected by a pressure sensor in much the same way as a heart beat, thereby tending to obscure the true heart beat.

Prior art attempts to deal with this problem have generally involved subtracting an electrical signal indicative of body movement generated by a first sensor from a composite signal indicative of heart beat plus body movement generated by a second sensor to determine the true heart beat. Such a technique is described in U.S. Pat. No. 4,063,551.

This technique, however, often yields erroneous heart beat information because the amplitude and phase of the body movement signal vary depending upon the body location where it is detected. For example, if a pressure sensor is placed on the user's finger to sense the pulsing of blood caused by the user's heart beat and body movement and an accelerometer sensor is placed on the user's wrist to sense only body movement and the user is running or jogging, the natural motion of the user's arm during running or jogging will cause blood to accumulate in the finger so that the amplitude of the body movement signal detected on the finger is greater than that detected on the wrist. Therefore, if the body movement signal detected on the wrist is subtracted from the composite heart beat plus body movement signal detected on the finger, differences in the amplitudes of the body movement components in the two signals will cause spurious peaks to appear in the resultant heart beat signal, which may be mistaken for actual heart beats. Thus, it will appear that the user's heart is beating faster than it actually is. Since the amplitude of the body movement signal detected on the finger can be two to three times that of the body movement signal detected on the wrist, errors in heart beat information can be significant.

SUMMARY OF THE INVENTION

It is therefore one object of the invention to provide an improved heart beat sensing and measuring instrument.

It is another object of the invention to provide an improved method of detecting an individual's heart beat and determining his heart rate.

It is yet another object of the invention to provide a portable, body-mountable instrument which is suitable for wear by one engaged in vigorous physical exercise.

It is still another object of the invention to provide a heart beat sensing and measuring instrument which is capable of accurately measuring the heart beat of an individual engaged in vigorous physical exercise.

It is a further object of the invention to provide an improved method of distinguishing an individual's true heart beat from a signal representing a composite of his heart beat and body movement.

These and other objects are accomplished in accordance with the present invention. A body-mountable instrument is provided having a first sensor for detecting pulsing of a user's blood resulting from the user's heart beat and body movement and for generating a first electrical signal indicative thereof and a second sensor for detecting the user's body movement and for generating a second electrical signal indicative thereof. The instrument further includes signal processing means responsive to the first and second electrical signals for determining the period of the second electrical signal and removing the body movement portion from the first signal in accordance with the determined period. In one embodiment means is provided for subtracting a first portion of the first electrical signal occurring during a first time interval from a corresponding second portion of the first electrical signal occurring during a second time interval. The second time interval is separated from the first time interval by a time period nt, where n is an integer and t is the period of the second electrical signal, so that the body movement component is removed from the first electrical signal, yielding the true heart beat signal.

In one embodiment, the instrument is comprised of a portable, wrist-mounted unit, which includes a digital processor for determining the user's heart beat based on elapsed time between successive beats and an accelerometer in contact with the user's wrist for sensing the periodic motion of the user's arm during exercise, and a finger-mounted unit, which includes a pressure sensor for sensing the pulsing of the user's blood resulting from heart beat and body movement and generating an electrical signal indicative thereof.

In a preferred embodiment the instrument includes an analog to digital converter for receiving analog input signals from the pressure sensor and accelerometer and for converting these analog signals into digital signals. A first digital processor is provided for receiving the digital signals from the analog to digital converter and determining the user's true heart beat and heart rate based on elapsed time between heart beats. A second digital processor is provided for computing various exercise-related parameters in accordance with a permanently stored instruction set based on heart beat and heart rate information and for controlling a visual display to display the results of selected computations performed by the second digital processor. In a further embodiment, the first and second digital processors may comprise a single processing means.

BRIEF DESCRIPTION OF THE DRAWINGS

Still further objects and advantages of the invention will be apparent from the Detailed Description and Claims when read in conjunction with the accompanying drawings wherein:

FIG. 4 is a flow diagram of the operation of the first digital processor to determine a user's true heart beat;

DETAILED DESCRIPTION OF THE INVENTION

Figure 1:
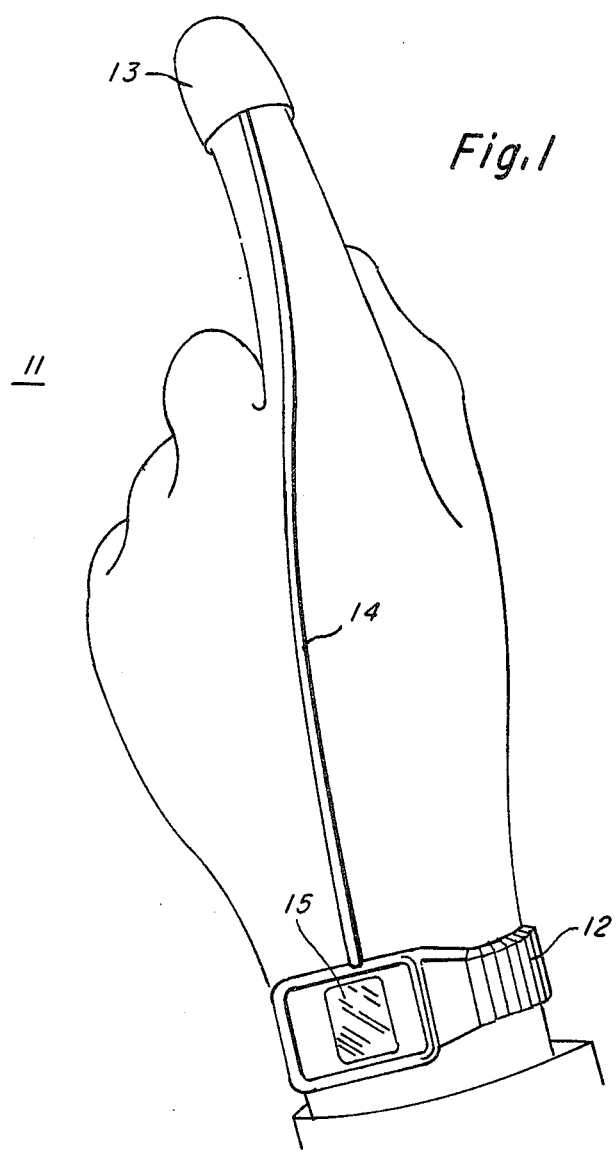
FIG. 1 is a perspective view of a heart beat measuring instrument of the present invention mounted on an individual's wrist and finger.

Referring to FIG. 1, a portable, body mountable instrument 11 for sensing and measuring heart beat is shown. Instrument 11 is comprised of a wrist-mounted unit 12, which contains the primary electronics of instrument 11, and a finger-mounted unit 13, which contains a pressure sensor for sensing the pulsing of the user's blood. Finger-mounted unit 13 is coupled to wrist-mounted unit 12 via an electrical wire 14. Wrist-mounted unit 12 resembles a typical wrist watch and includes timekeeping circuitry for keeping track of elapsed time and processing circuitry for determining the heart beat and heart rate of the user based on information signals received from the pressure sensor contained in finger-mounted unit 13 and a body movement sensor (not shown) disposed on wrist-mounted unit 12 for detecting the body movement of the user.

The pressure sensor is preferably comprised of a piezoelectric transducer positioned in contact with one of the user's fingers for detecting pressure variations caused by the user's heart beat plus body movement and generating a first electrical signal indicative thereof. The body movement sensor is preferably an accelerometer which senses the movement of the user's arm during physical activity and generates a second electrical signal indicative thereof. The body movement signal generated by the accelerometer is primarily the result of the natural motion of the user's arm during physical exercise. For example, when one is running or jogging, his arms tend to move back and forth in a periodic motion dependent upon the pace at which he is running and hence the frequency at which either foot hits the ground. The back and forth movement of the user's arm also causes his blood to pulse in sequence with the arm movement so that both the piezoelectric transducer and the accelerometer generate body movement signals in synchronism with the user's feet hitting the ground. For this reason, the body movement signal is commonly referred to as the "footfall" signal. The fundamental period of the footfall signal is typically the time interval between successive hits of one of the user's feet.

Wrist-mounted unit 12 further includes a visual display 15 for displaying heart beat, elapsed time and other exercise-related information of interest to the user. Display 15 is preferably a low power digital display, such as, for example, a liquid crystal display.

Figure 2:
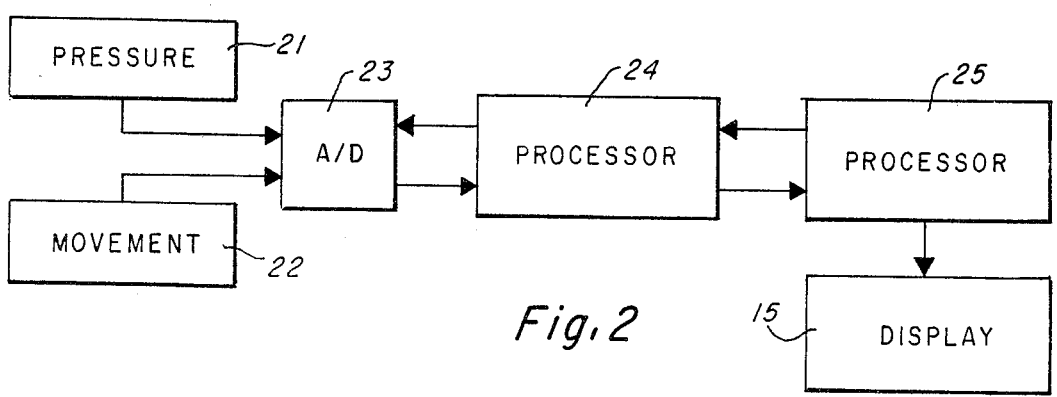
FIG. 2 is a block diagram of the major components of the heart beat measuring instrument.

The major components of instrument 11 are depicted in FIG. 2. Pressure sensor 21 senses the pulsing of blood in the user's finger and generates a heart beat plus footfall electrical signal, which is transmitted to an analog to digital (A/D) converter 23, and accelerometer 22 senses the motion of the user's arm and generates a footfall signal, which is also transmitted to A/D converter 23. A/D converter 23 periodically converts the analog heart beat plus footfall signal and the analog footfall signal into respective digital signals and transmits the digital signals to a first digital processor 24. First digital processor 24, which contains timekeeping circuitry for keeping track of elapsed time, removes the footfall component from the composite heart beat plus footfall signal to arrive at the user's true heart beat. The heart rate is then computed by first digital processor 24 based on elapsed time between successive heart beats. A/D converter 23 is preferably a switch capacitor A/D converter, such as TL 520, and first digital processor 24 is preferably a microcomputer, such as a TP0455, both of which are manufactured and sold as standard products by Texas Instruments Incorporated, assignee of the present invention.

In the present embodiment, heart rate information is transmitted by first digital processor 24 to a second digital processor 25, (also preferably a microcomputer, such as the TP0455), which is responsive to the information for computing a variety of exercise-related parameters for which instrument 11 is programmed, although it is contemplated that the functions of first and second digital processors 24 and 25 may be combined into a single digital processor. Second digital processor 25 also controls display 15 for selectively displaying information to the user. In one embodiment, second digital processor 25 is programmed to calculate velocity and distance traveled by an individual during an exercise period based on the user's heart rate and number of heart beats occurring during the exercise period, as described and claimed in No. 4,312,358 which is assigned to the assignee of the present invention and is hereby incorporated herein by reference.

Figure 3A:
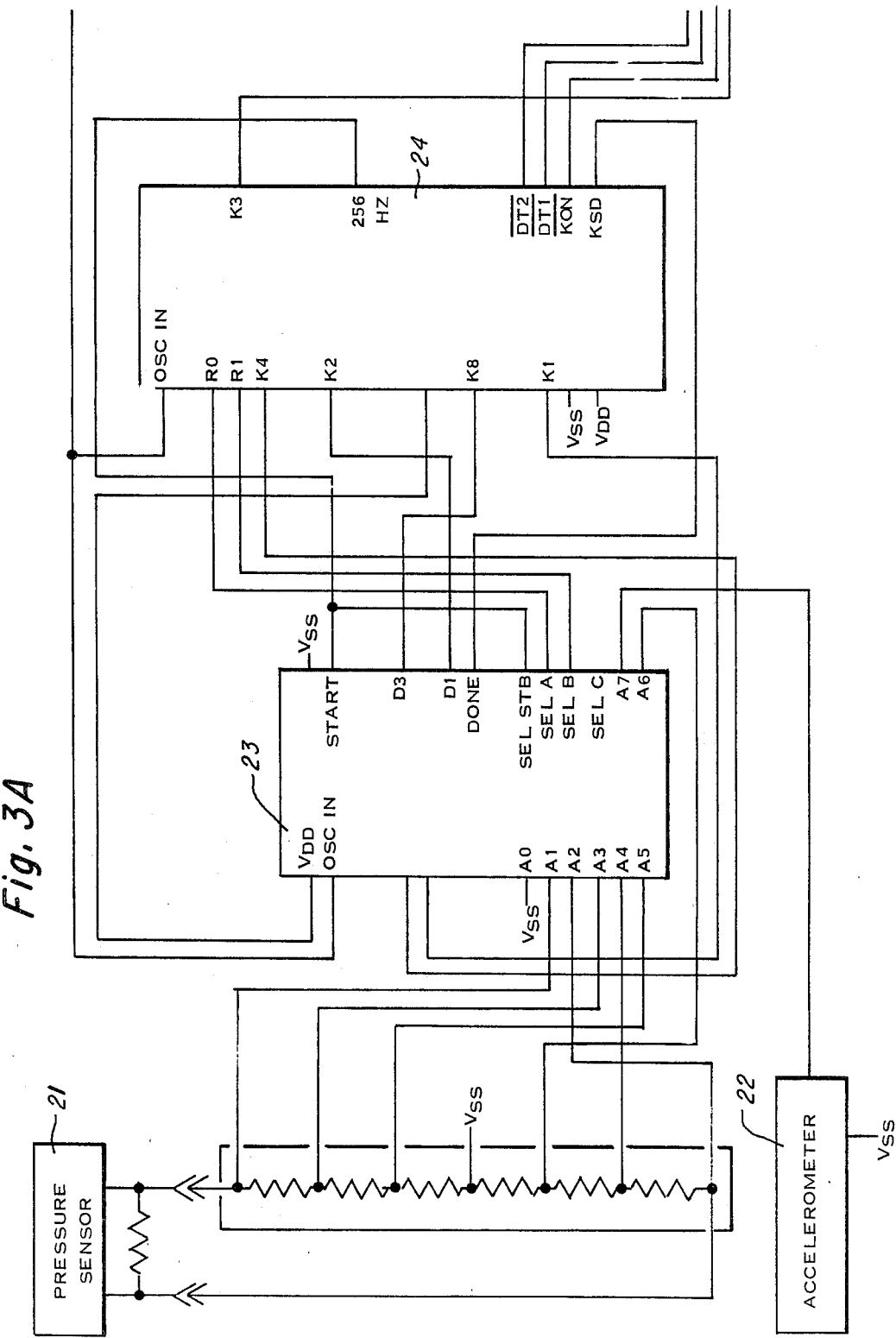
FIGS. 3a and 3b are circuit diagrams of the heart beat measuring instrument.
Figure 3B:
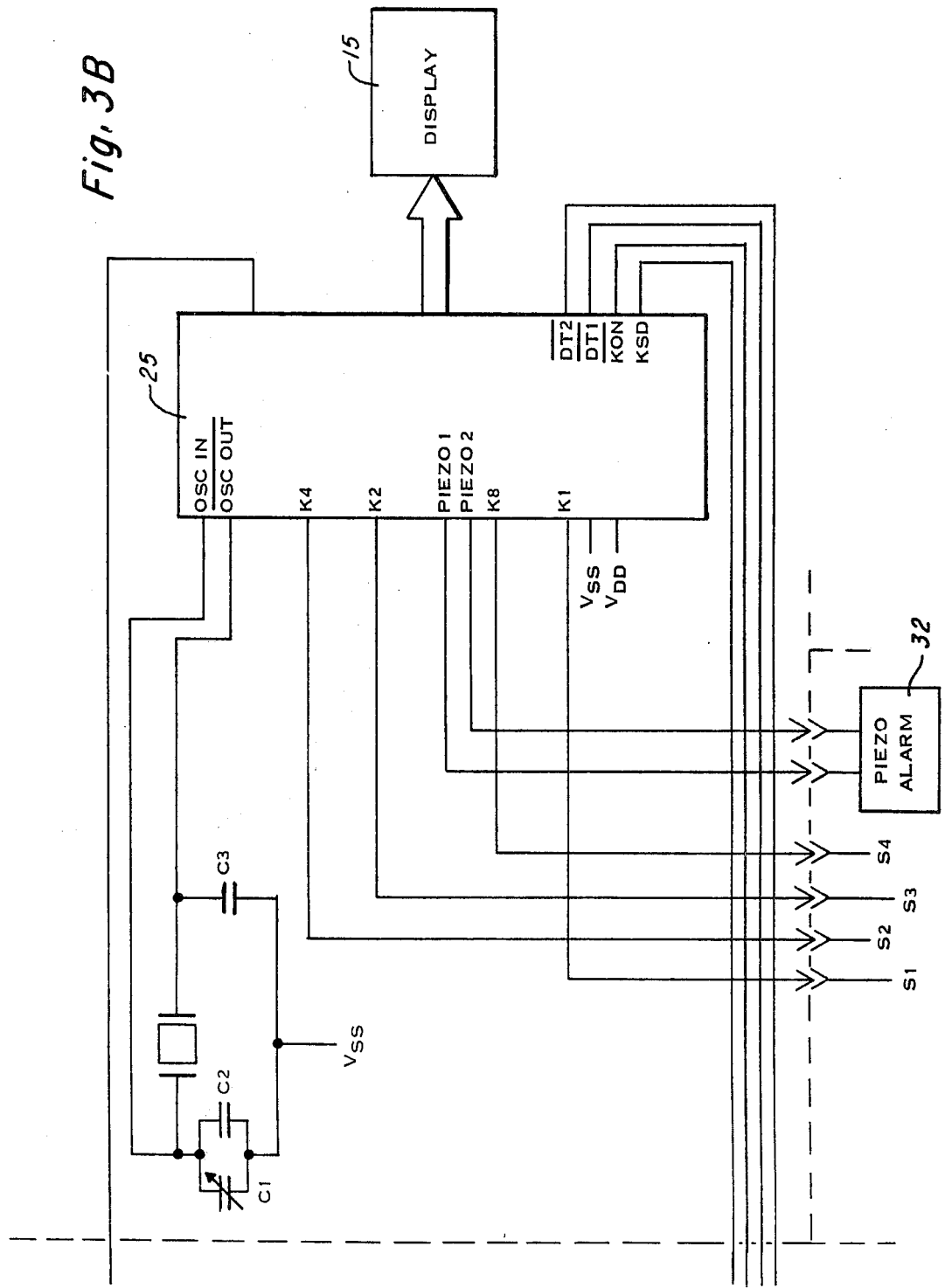

Referring to FIGS. 3a and 3b, first digital processor 24 generates a 256 Hz signal which is received by A/D converter 23 on the START input pin and the SELECT STROBE (SEL STB) input pin to trigger A/D converter 23 into operation and to indicate that the binary coded signals received on inputs SEL A, SEL B and SEL C are valid. A/D converter 23 receives the heart beat plus footfall signal on selected ones of input pins A1–A6, the footfall signal on input pin A7 and a reference voltage Vss, which corresponds to ground potential, on input pin A0 in a sequence dictated by first digital processor 24. First digital processor 24 generates a 3-bit binary coded signal on output pins R0, R1 and R2 every 1/256 second, which indicates the respective input pin being selected. The 3-bit binary coded signal is received on respective input pins SEL A, SEL B and SEL C of A/D converter 23. The sequence is such that every 1/64 second, A/D converter 23 performs four separate conversions—two conversions of the heart beat plus footfall signal, one conversion of the footfall signal and one conversion of Vss reference voltage signal.

A/D converter 23 converts the analog signals into respective 4-bit digital words and generates a DONE signal after each conversion, indicating that the particular conversion has been completed and that the data which follows is valid. The digital words are transmitted on output pins D0–D3 and received by first digital processor 24 on respective input pins K1, K2, K4 and K8.

A resistor divider circuit 31 is interposed between pressure sensor 21 and A/D converter 23 to provide multiple input paths for the heart beat plus footfall signal into A/D converter 23 at different levels of attenuation. Divider circuit 31 includes a bank of resistors in series and a voltage center tap for providing a reference voltage, Vss. This allows the gain of the signal to be adjusted so that the signal amplitude is within the range covered by a 4-bit data word. Also, because A/D converter 23 converts only signals of positive polarity, the original heart beat plus footfall signal at a selected attenuation level is fed to A/D converter 23 on one input and an inverted version of the signal at the same attenuation level is fed to A/D converter 23 on another input so that the entire heart beat plus footfall signal can be converted to digital form. First digital processor 24 controls the gain of the heart beat plus footfall signal by activating selected pairs of input pins A1–A6 of A/D converter 23 and cooperates with divider circuit 31 to provide an automatic gain control (AGC) function. The sequence of operation of first digital processor 24 to select the appropriate gain of the heart beat plus footfall signal will be described in more detail below.

Figure 3C:
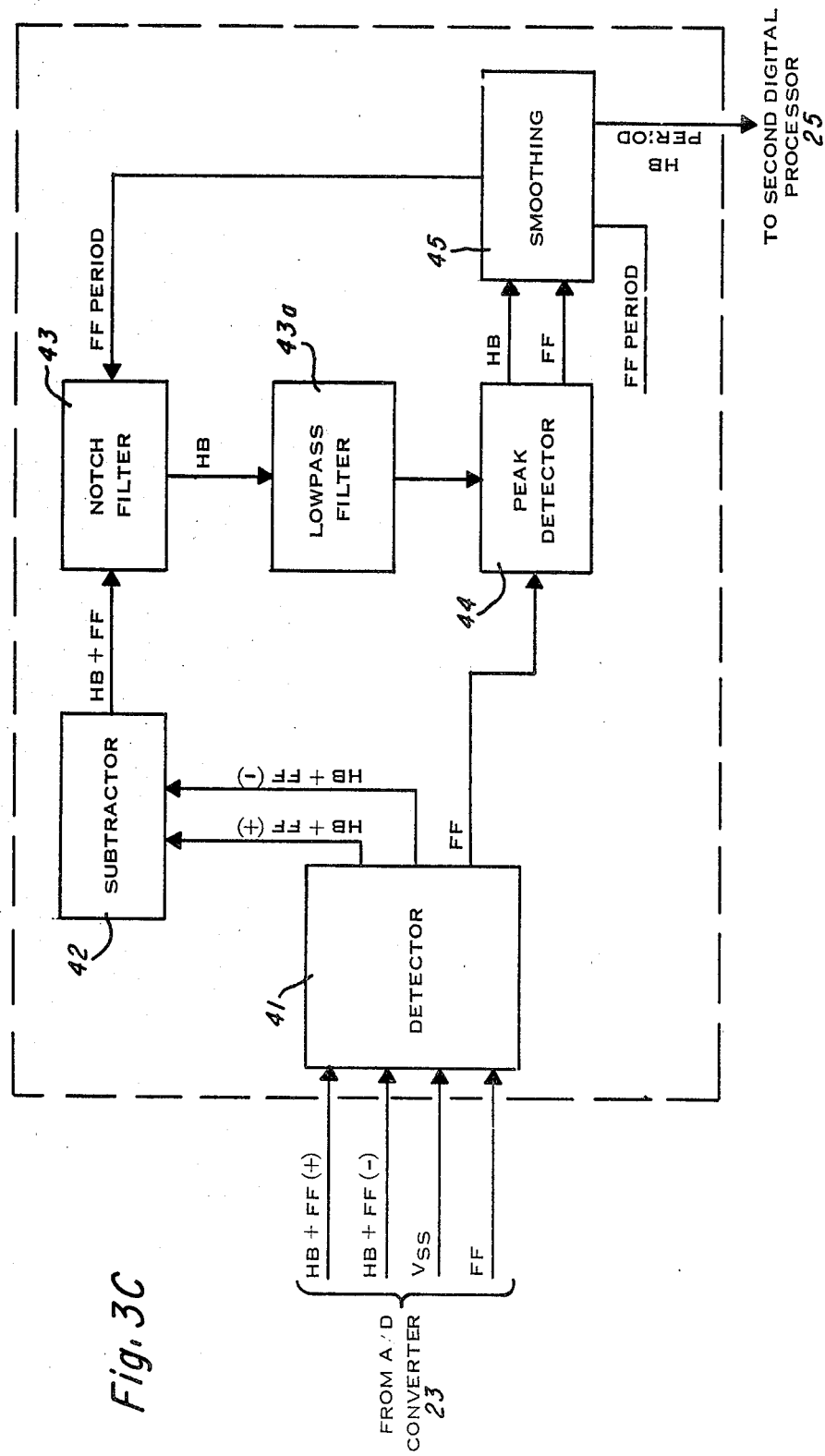
FIG. 3c is a block diagram of the major functional components of a first digital processor contained in the heart beat measuring instrument.

Referring to FIG. 3c, first digital processor 24 receives four signals from A/D converter 23—the positive portion of the original heart beat plus footfall signal (HB+FF(+)); the positive portion of the inverted heart beat plus footfall signal (HB+FF(−)); the Vss reference voltage signal; and the footfall signal (FF). The four signals are received by a signal detector circuit 41, which measures the amplitudes of the original and inverted signals for AGC purposes. The original bipolar heart beat plus footfall signal is reconstructed in subtractor circuit 42 by subtracting the positive portion of the inverted signal from the positive portion of the original signal. The bipolar signal (HB+FF) is then transmitted to a notch filter 43 where the signal is stored and the footfall component is removed from the heart beat plus footfall signal.

The resultant heart beat signal is sent to a low pass filter 43a wherein excess noise is filtered out and then to a peak detector circuit 44 which detects amplitude peaks in the signal. When a peak is detected, the time period elapsed since the last detected peak is computed and this value is "smoothed", i.e. averaged, together with a previous average heart beat period in a smoothing circuit 45 to yield a current average beat period (HB Period), which is transmitted to second digital processor 25.

Peak detector circuit 44 also detects amplitude peaks in the footfall signal. When a peak is detected, the time period elapsed since the last detected peak is computed and this value is smoothed together with a previous average footfall period to yield a current average footfall period (FF Period). The current average footfall period is transmitted to notch filter 43 and is used to remove the footfall component from the heart beat plus footfall signal, as will be described in greater detail below. The sequence of operation of first digital processor 24 to determine the true heart beat and period between heart beats will be best understood with reference to FIGS. 4–10.

Referring to FIG. 4, first digital processor 24 receives the positive portion of the original signal (+) and the positive portion of the inverted signal (−), checks the amplitudes of the signals for AGC purposes and reconstructs the original bipolar heart beat plus footfall (HB+FF) signal, as described above. If instrument 11 is set in a RUNNING mode, i.e. the user is engaged in physical exercise, the heart beat plus footfall signal is sent to the notch filter wherein the footfall component of the heart beat plus footfall signal is removed. This is acomplished by subtracting a first portion of the heart beat plus footfall signal occurring during a first time interval from a corresponding second portion occurring during a second time interval, the first and second time intervals being separated by time period equivalent to nt, where n is an integer and t is the period of the footfall signal. Those skilled in the art will appreciate that the amplitude and phase of the footfall component are substantially identical in corresponding portions of the heart beat plus footfall signal which occur at time intervals equivalent to integer multiples of one footfall period apart. In a preferred embodiment, a previous heart beat plus footfall signal delayed by one footfall period (n=1) is subtracted from the current heart beat plus footfall signal to remove the footfall component and provide a true indication of the user's heart beat.

Figure 5:
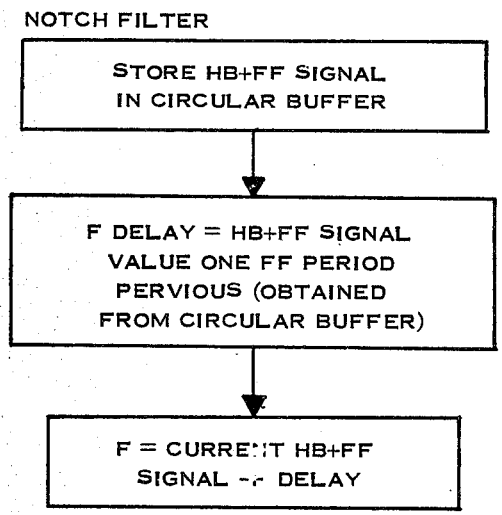
FIG. 5 is a flow diagram showing the removal of the body movement component from the composite heart beat plus body movement signal within the first digital processor.
Figure 6:
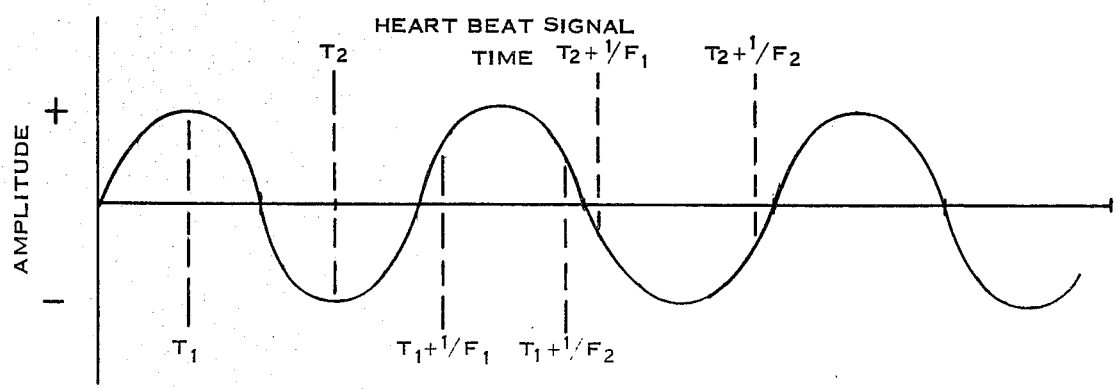
FIG. 6 is an amplitude versus time graph of a user's heart beat signal after the signal has been processed by the first digital processor.
Figure 7:
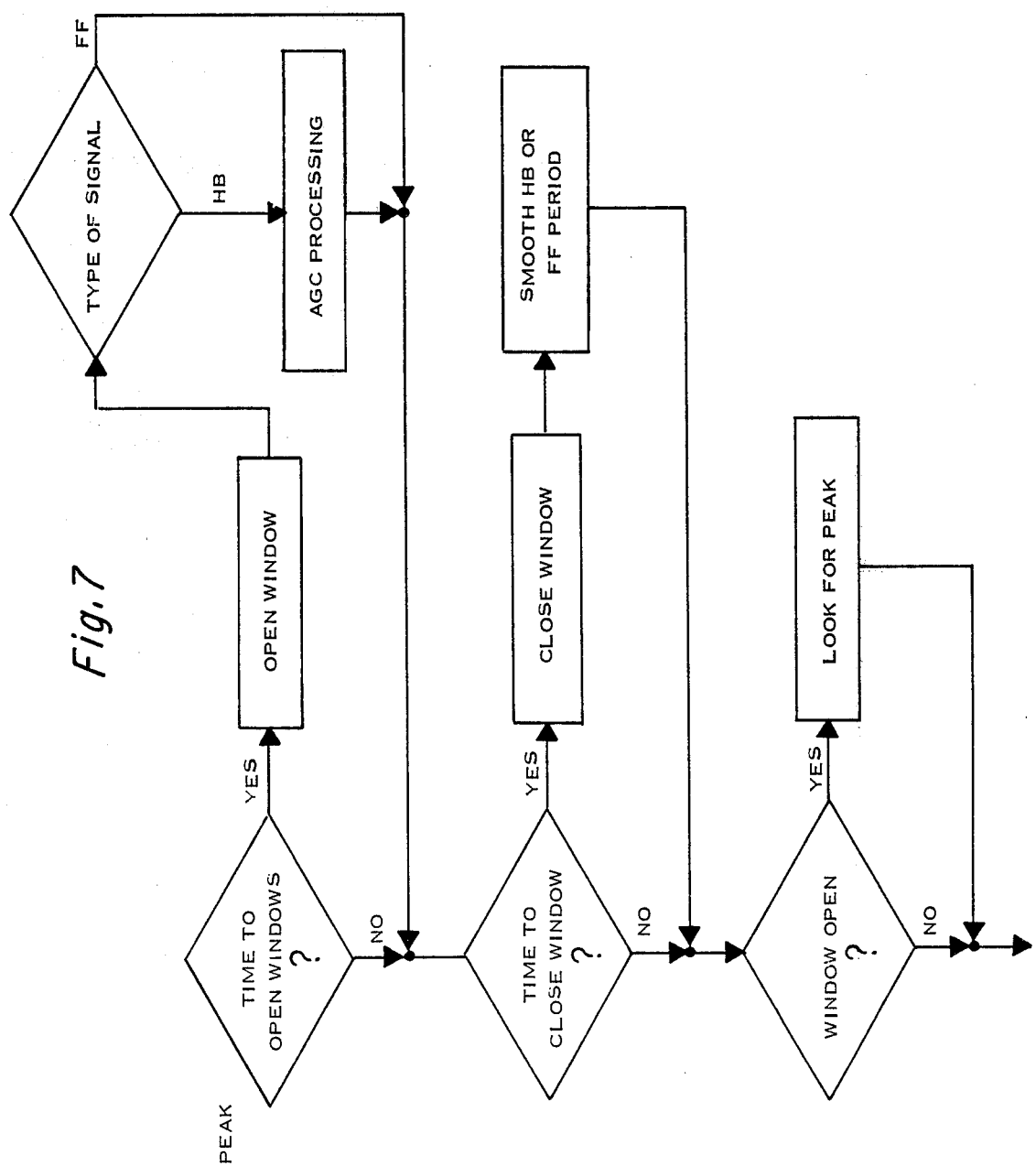
FIG. 7 is a flow diagram depicting the detection of peaks in the heart beat signal and in a body movement signal within the first digital processor.

Referring also to FIG. 5, the processing of the heart beat plus footfall signal in the notch filter is shown in greater detail. The signal is stored in sequence in a 64-word circular buffer. Each word storage location in the buffer accomodates a 4-bit data word representing the heart beat plus footfall signal during a respective 1/64 second time interval. The buffer includes a read pointer which is set at a location corresponding to one footfall period in time removed from the location of a write pointer where the current heart beat plus footfall signal is being stored. Both the read and write pointers are advanced one location after each 1/64 second cycle to maintain the desired delay. The delayed signal at the read pointer location is subtracted from the current signal at the write pointer location to remove the footfall component of the heart beat plus footfall signal and provide a signal indicative of the user's heart beat.

The signal is then low pass filtered to remove excess noise. If instrument 11 is not in the RUNNING mode, the signal bypasses the notch filter and goes directly to the low pass filter. After the signal is low pass filtered, it resembles a sine wave (see FIG. 6), the period of which corresponds to the user's heart rate. However anomalies are often present in the signal which cause it to depart from a true sine wave waveform. To overcome this problem, the heart beat period is determined by detecting peaks in the heart beat signal and averaging the currently measured time interval between peaks with the time interval previously computed. First digital processor 24 looks for the positive and negative peaks in the heart beat plus footfall signal in accordance with the sequence depicted in FIG. 7. A peak occurs at the point of maximum signal amplitude within a prescribed time window, as best seen in conjunction with FIG. 6. The time window is referenced from the last detected peak so that when the window opens, first digital processor 24 begins looking for the next peak and when the window closes, first digital processor 24 ceases looking for the peak. The time window is chosen based on the minimum and maximum heart rates anticipated for the particular mode of operation of instrument 11. Thus, the window would open at time $t + 1/f_1$ and close at time $t + 1/f_2$, where t is time of occurrence of the last detected peak, $f_1$ is the maximum heart rate and $f_2$ is the minimum heart rate. For example, when instrument 11 is in the RUNNING mode, the time window opens at $t + 19/64$ second and closes at $t + 37/64$ second. This corresponds to a minimum heart rate of 103 beats per minute and a maximum heart rate of 202 beats per minute, which encompasses the range in which an individual's heart rate is most likely to fall during exercise. A different time window is of course chosen when an individual is not engaged in physical exercise since his heart rate is likely to be much lower. To ensure that only one peak occurs within each time window, the ratio of f1/f2 must be no greater than 2.

Figure 8:
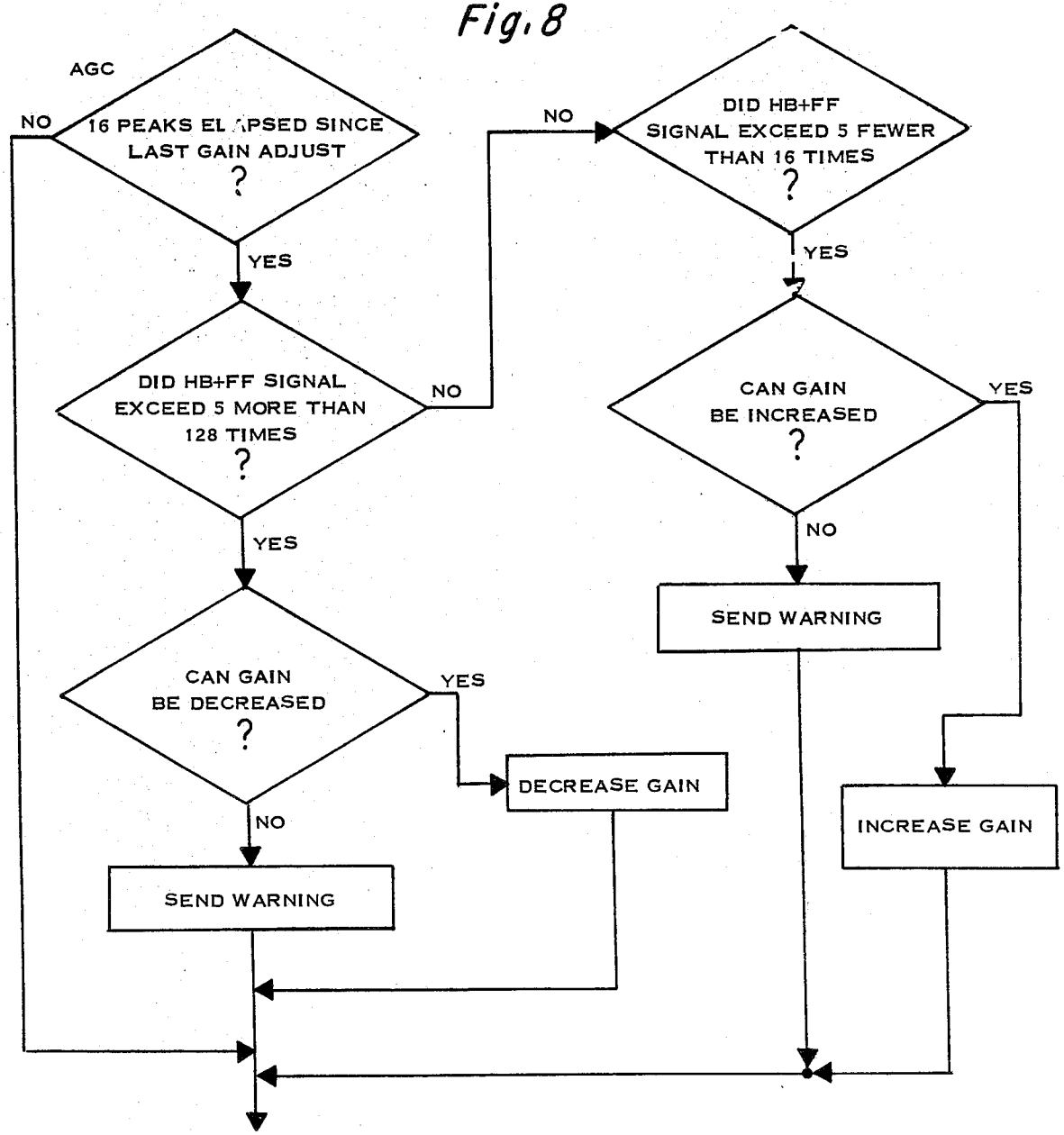
FIG. 8 is a flow diagram of the automatic gain control function for varying the amplitude of the incoming signal from the finger-mounted sensor shown in FIG. 1.

In addition to detecting the peaks in the heart beat signal, first digital processor 24 also determines whether the gain of the signal needs to be adjusted in accordance with the sequence set forth in FIG. 8. Referring to FIG. 8, the gain cannot be adjusted until at least 16 peaks have been detected since the last gain adjustment. If at least 16 peaks have been detected, the gain will be adjusted downward if the heart beat plus footfall signal exceeded a binary 5 (0101) more than 128 times and will be adjusted upward if the signal exceeded a binary 5 fewer than 16 times since the last gain adjustment. If first digital processor 24 determines that a gain adjustment is necessary, but no further adjustment can be made, a warning signal is transmitted to second digital processor 25, which activates a piezoelectric alarm 32 (FIG. 3b) in response to the warning signal, thereby indicating to the user that the heart beat signal is either excessively high or low.

Figure 9:
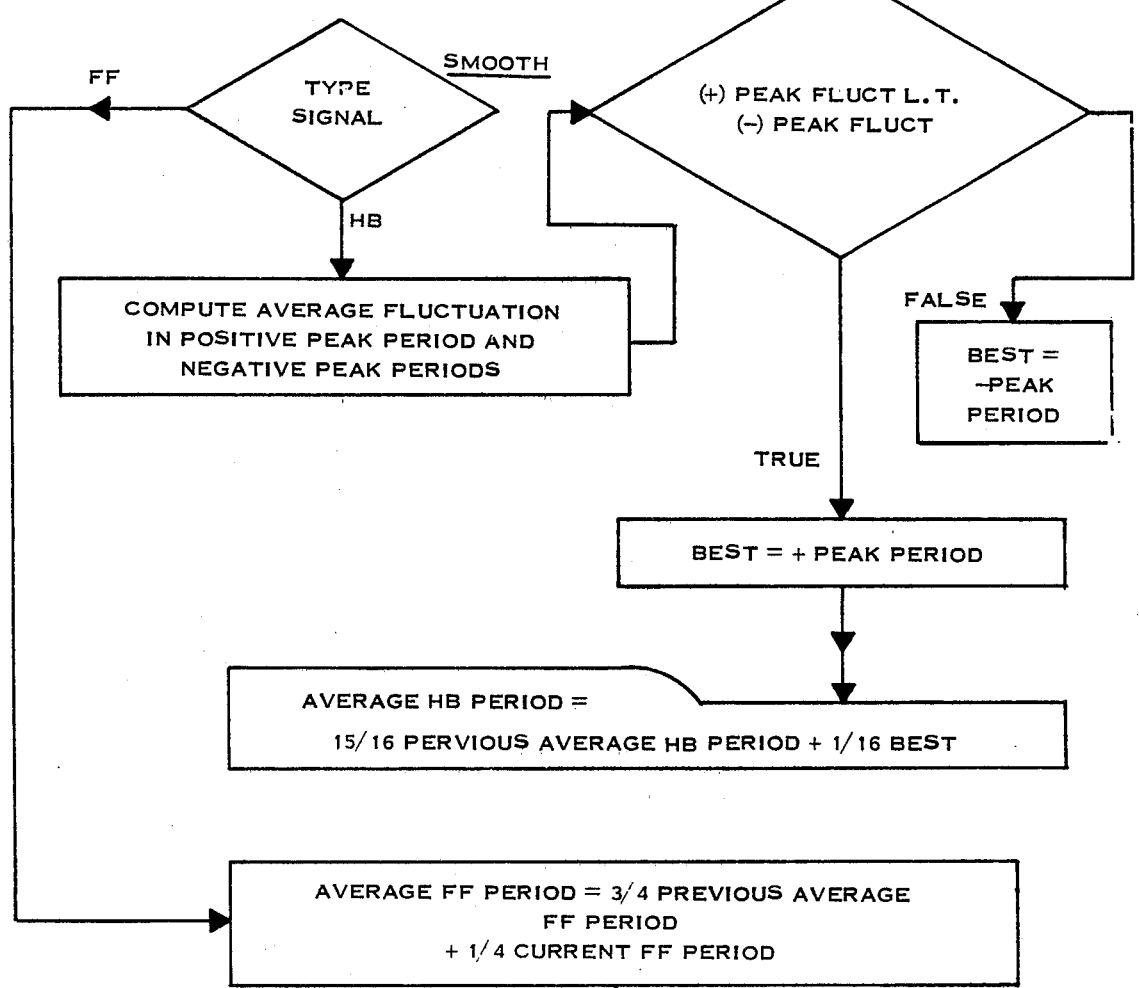
FIG. 9 is a flow diagram showing the smoothing operation which occurs within the first digital processor whereby an average heart beat period is determined.

Referring again to FIG. 7, when first digital processor 24 detects that it is time to close the window, it ceases looking for peaks and computes heart beat period in accordance with FIG. 9. To compute the period between heart beats, the currently measured heart beat period must be smoothed together with the previous average heart beat period. The average heart beat period is initially assumed to be 0.6 second, i.e. a heart rate of 100 beats per minute, and is updated during each 1/64 second cycle based on the heart beat periods computed during the previous cycles. First digital processor 24 first computes the average fluctuation in the positive and negative peak periods. The average fluctuation is determined by computing the magnitude of the difference between the currently measured heart beat period and the heart beat period measured during the preceding cycle and averaging this magnitude together with the corresponding magnitude computed for the two cycles prior to that so that the average fluctuation represents variations in the heart beat period computed over the last four cycles. The average fluctuations for both the positive and negative peak information are determined and first digital processor 24 selects the particular peak information having the lesser fluctuation to compute the period between heart beats. The new average heart beat period is computed as follows:

New average heart beat period = currently measured heart beat period x A + previous average heart beat period xf1 − A), where A is a constant which determines the degree of smoothing.

It has been found that a proper value of A should be in the range 1/16 to 1/8 with 1/16 representing the optimum value for reducing estimation noise.

Figure 10:
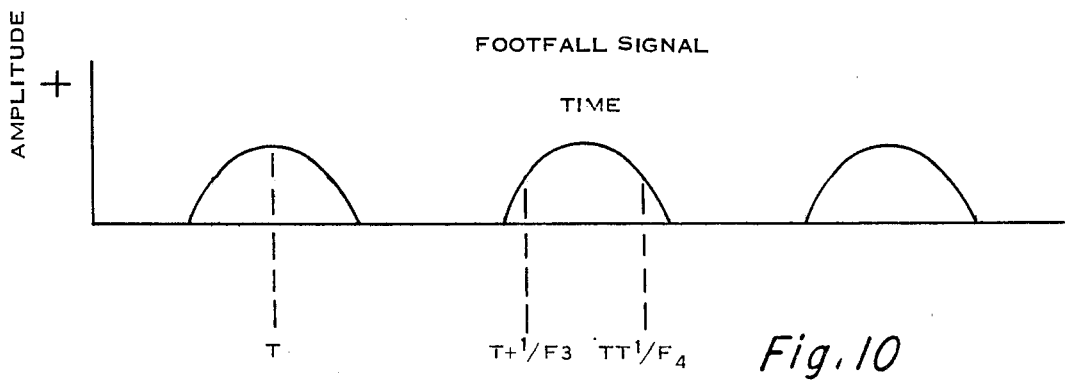
FIG. 10 is an amplitude versus time graph showing the positive portion of the body movement signal.

The footfall signal, which is illustrated in FIG. 10, is processed in much the same as the heart beat signal as shown in FIGS. 8 and 9, except that no gain adjustment is made in the footfall signal and only positive peak information is available. Also, the time window selected for the footfall signal is different from that of the heart beat signal so that the window opens at time $t + 1/f_3$ and closes at time $t + 1/f_4$, where t is the time of occurrence of the last footfall peak, $f_3$ is the maximum footfall rate and $f_4$ is the minimum footfall rate. For example, when instrument 11 is in a RUNNING mode, the window opens at $t + 37/64$ second after the last detected peak and closes at $t + 58/64$ second. The new average footfall period is computed as follows:

New average footfall period = currently measured footfall period x B + previous average footfall period x (1 − B) where B is a constant which determines the degree of smoothing.

It has been found that a proper value of B is between 1/8 and 1/4 with 1/4 being selected for optimum dynamic response. The new average footfall period is used during the next cycle to set the read pointer in the 64 word circular buffer for the desired delay period. The footfall period is initially assumed to be on the order of 0.78 second, which corresponds to a footfall rate of 76.8 times per minute. The footfall period is updated during each 1/64 second cycle.

Referring again to FIG. 3b, heart rate information is transmitted via output pins DT 1 and DT 2 of first digital processor 24 to input pins Kon and Ksd of second digital processor 25, wherein the information is used to compute various exercise-related parameters. Second digital processor 25 indicates that it has received the information by transmitting coded signals via output pins DT1 and DT2, which are received via input pins Kon and K3, respectively, of first digital processor 24.

Second digital processor 25 receives input signals on pins K1, K4, K2 and K8 indicative of the respective states of user-controllable switches S1, S2, S3, and S4, which are located on the exterior of heart beat sensing and measuring instrument 11. Switches S1-S4 are used to select and control the mode of operation of instrument 11 and to allow the user to display selected information on display 15.

Various embodiments of the invention have now been described in detail. Since it is obvious that many additional changes and modifications can be made in the above-described details without departing from the nature and spirit of the invention, the invention is not to be limited to these details except as set forth in the appended claims.

What is claimed is:

1. A body-mountable instrument for detecting and measuring heart beat of a user, comprising:
   (a) first sensor means for detecting pulsing of the user's blood resulting from the user's heart beat and body movement and generating a first electrical signal indicative thereof;
   (b) second sensor means for detecting the user's periodic body movement and generating a second electrical signal indicative thereof; and
   (c) processing means responsive to said first and second electrical signals for determining the period of the second electrical signal and for subtracting a first portion of the first electrical signal occurring during a first time interval from a corresponding second portion of said first electrical signal occurring during a second time interval, said first and second time intervals being separated by a time period equivalent to nt, where n is an integer and t is the period of said second electrical signal, thereby separating body movement from heart beat in the first electrical signal.

2. The instrument according to claim 1 wherein the period of the second electrical signal corresponds to the rate at which the user's feet hit the ground during physical activity.

3. The instrument according to claim 1 wherein said first portion of said first electrical signal precedes said second portion thereof by a time period equivalent to t, said second portion being the most recently occurring portion of said first electrical signal.

4. The instrument according to claim 1 wherein said first sensor means is comprised of a piezoelectric transducer for sensing pressure variations caused by the pulsing of the user's blood and for converting said pressure variations into said first electrical signal.

5. The instrument according to claim 4 wherein said piezoelectric tranducer is mounted on one of the user's fingers.

6. The instrument according to claim 1 wherein said second sensor means is comprised of an accelerometer for detecting the user's body movement and converting said body movement into said second electrical signal indicative thereof.

7. The instrument according to claim 6 wherein said accelerometer is mounted on one of the user's wrists.

8. The instrument according to claim 1 wherein said processing means is comprised of:
   (i) analog to digital converter means for receiving said first and second electrical signals in analog form and for converting said analog signals into digital signals; and
   (ii) first digital processor means responsive to said digital signals for determining the user's heart beat.

9. The instrument according to claim 8 further including a resistor divider circuit coupled between said first sensor means and said analog to digital converter means for providing selected amounts of attenuation of said first electrical signal, the amount of attenuation being selected by said first digital processor means to control the gain of the first electrical signal.

10. The instrument according to claim 9 wherein said analog to digital converter means converts said first electrical signal and a third electrical signal corresponding to the inverse of said first electrical signal into respective four bit digital data words, said data words representing the amplitude of the respective signals during respective 1/64 second time intervals.

11. The instrument according to claim 8 further including a second digital processor means responsive to heart beat information computed by said first digital processor means for calculating a plurality of exercise-related parameters in accordance with a permanently stored instruction set.

12. The instrument according to claim 11 further including display means for displaying the results of selected computations performed by said first and second digital processor means to the user, said display means being selectively controlled by said second digital processor means.

13. A method of detecting and measuring an individual's heart beat, comprising the steps of:
   (a) mounting first and second sensor means on selected portions of the individual's body, said first sensor means for detecting pulsing of the individual's blood resulting from his heart beat and periodic body movement and for generating a first electrical signal indicative thereof, said second sensor means for detecting the individual's body movement and for generating a second electrical signal indicative thereof;
   (b) determining the period of the individual's body movement from the second electrical signal; and
   (c) subtracting a first portion of the first electrical signal occurring during a first time interval from a corresponding second portion of the first electrical signal occurring during a second time interval, said first and second time intervals being separated by a time period equivalent to nt, where n is an integer and t is the period of the second electrical signal, so that body movement is separated from heart beat in the first electrical signal.

14. A method according to claim 13 wherein the period of the second electrical signal corresponds to the rate at which the user's feet hit the ground during physical activity.

15. A method according to claim 13 wherein the first portion of said first electrical signal precedes the second portion thereof by a time period equivalent to t, said second portion being the most recently occurring portion of the first electrical signal.

16. A method according to claim 13 wherein said first and second electrical signals are analog signals and said method includes the step of converting said first and second electrical signals into respective first and second digital signals.

17. A method according to claim 16 further including the step of selectively controlling the gain of said first electrical signal, said step comprising the substeps of:
   (i) measuring the amplitude of the first digital signal at selected time intervals;
   (ii) counting the number of occurrences within a predetermined time period in which the measured amplitude exceeded a predetermined threshold value;
   (iii) comparing said number of occurrences with predetermined first and second numbers, said second number being greater than said first number; and
   (iv) adjusting the gain of said first digital signal upward if said number of occurrences is less than said first number and adjusting the gain of said first digital signal downward if said number of occurrences exceeds said second number.

18. A method according to claim 17 wherein said gain is adjusted by selectively attenuating said first digital signal by predetermined amounts.

19. A method according to claim 13 further including the step of computing an average heart beat period, based on a current heart beat period and a previous average heart beat period, comprising the substeps of:
   (i) detecting the occurrence of amplitude peaks of positive and negative polarity in an electrical signal indicative of heart beat;
   (ii) determining respective current heart beat periods by measuring elapsed time periods between a currently measured peak and an immediately preceding peak of the same polarity for both the positive and negative peaks;
   (iii) comparing said current heart beat periods with corresponding previous heart beat periods determined for a predetermined number of previous positive and negative peaks;
   (iv) selecting the current heart beat period corresponding to the particular one of the positive and negative peaks having a lesser average variation in heart beat periods computed over the number of peaks compared; and
   (v) smoothing the selected current heart beat period with the previous average heart beat period to determine the average heart beat period in accordance with the following:
   average heart beat period = A x selected current heart beat period + (1 − A) x previous average heart beat period where A is a constant representing the degree of smoothing between the current heart beat period and the previous average heart beat period.

20. A method according to claim 19 wherein said substep of detecting the occurrence of amplitude peaks is comprised of detecting a point of maximum amplitude in the electrical signal within a selected time interval, beginning at a first predetermined time after the occurrence of the last detected amplitude peak and ending at a second predetermined time after the occurrence of the last detected amplitude peak, said time interval being selected in accordance with selected maximum and minimum heart beat periods.

21. A method according to claim 19 further including the step of determining an average body movement period based on a current body movement period and a previous average body movement period, comprising the substeps of:
   (i) detecting the occurrence of amplitude peaks in the second electrical signal;
   (ii) determining current body movement period by measuring an elapsed time period between a currently measured peak and an immediately preceding peak; and
   (iii) smoothing the current body movement period with the previous average body movement period in accordance with the following: average body movement period = B x current body movement period + (1 − B) x previous average body movement period, where B is a constant representing the degree of smoothing between the current body movement period and the previous average body movement period.

22. An instrument for detecting heart beat of a user, comprising:
   (a) first sensor means for detecting pulses of the user's blood resulting from the user's heart beat and the user's periodic body movement and for generating a first electrical signal indicative thereof;
   (b) second sensor means for detecting the user's periodic body movement and generating a second electrical signal indicative thereof; and
   (c) signal processing means including:
      (i) means for determining the period of the user's periodic body movement from said second electrical signal; and
      (ii) means for substracting a first portion of the said first electrical signal from a second corresponding portion of said first electrical signal in accordance with the determined body movement period to generate a third electrical signal indicative of heart beat alone.

23. A method of detecting heart beat of a user comprising:
   (a) detecting pulses of the user's blood resulting from the user's heart beat and periodic body movement and generating a first electrical signal indicative thereof;
   (b) detecting the user's periodic body movement and generating a second electrical signal indicative thereof;
   (c) determining the period of the user's body movement from said second electrical signal; and
   (d) subtracting a first portion of the first electrical signal from a second corresponding portion of the first electrical signal in accordance with the determined body movement period to generate a third electrical signal indicative of heart beat alone.

* * * * *